United States Patent [19]

Tjahaja et al.

[11] Patent Number: 5,065,459
[45] Date of Patent: Nov. 19, 1991

[54] DISPOSABLE PORTABLE URINAL

[76] Inventors: Surja Tjahaja, 3343 Brittan Ave., #4, San Carlos, Calif. 94070; Robert L. Nodvik, 2805 Kerckhoff St., San Pedro, Calif. 90731

[21] Appl. No.: 530,108

[22] Filed: May 3, 1990

[51] Int. Cl.⁵ ............................................. A47K 11/00
[52] U.S. Cl. ..................................... 4/144.2; 4/144.3
[58] Field of Search .................. 4/144.1, 144.2, 144.3, 4/484, 144.4, 451, 452; 128/760, 763, 767; 604/317, 327, 332, 336, 338, 339, 341; 383/88, 89

[56] References Cited

U.S. PATENT DOCUMENTS

| 2,878,486 | 3/1959 | Barlett et al. | 4/144.4 |
|---|---|---|---|
| 3,200,415 | 8/1965 | Breece, Jr. | 4/144.3 |
| 3,292,626 | 12/1966 | Schneider | 383/89 |
| 3,295,145 | 1/1967 | Ericson | 4/144.3 |
| 3,406,690 | 10/1968 | Igel et al. | 128/767 |
| 3,523,537 | 8/1970 | Hill | 128/295 |
| 3,746,240 | 7/1973 | Flynn | 220/462 |
| 4,023,216 | 5/1977 | Li | 4/110 |
| 4,188,989 | 2/1980 | Anderson | 150/9 |
| 4,197,849 | 4/1980 | Bostick | 128/295 |
| 4,204,527 | 5/1980 | Wu et al. | 128/762 |
| 4,294,582 | 10/1981 | Naslund | 23/230 B |
| 4,406,659 | 9/1983 | Broida | 604/339 |
| 4,790,834 | 12/1988 | Austin | 604/349 |
| 4,871,265 | 10/1989 | Peck | 383/89 |

FOREIGN PATENT DOCUMENTS 2936622 3/1981 Fed. Rep. of Germany.

Primary Examiner—Henry J. Recla
Assistant Examiner—David J. Walczak
Attorney, Agent, or Firm—Limbach, Limbach & Sutton

[57] ABSTRACT

A disposable portable urinal for males comprising a collapsible cylindrical collar having the perimeter of one end sealably attached to a receptacle for deposit of fluilds therein. The collar has handle tabs attached to its exterior surface to facilitate gripping. An adhesive strip is attached to the exterior of the collar. Score lines located on the surface of the collar allow the collar to be laterally collapsed and longitudinally folded and sealed upon itself.

8 Claims, 2 Drawing Sheets

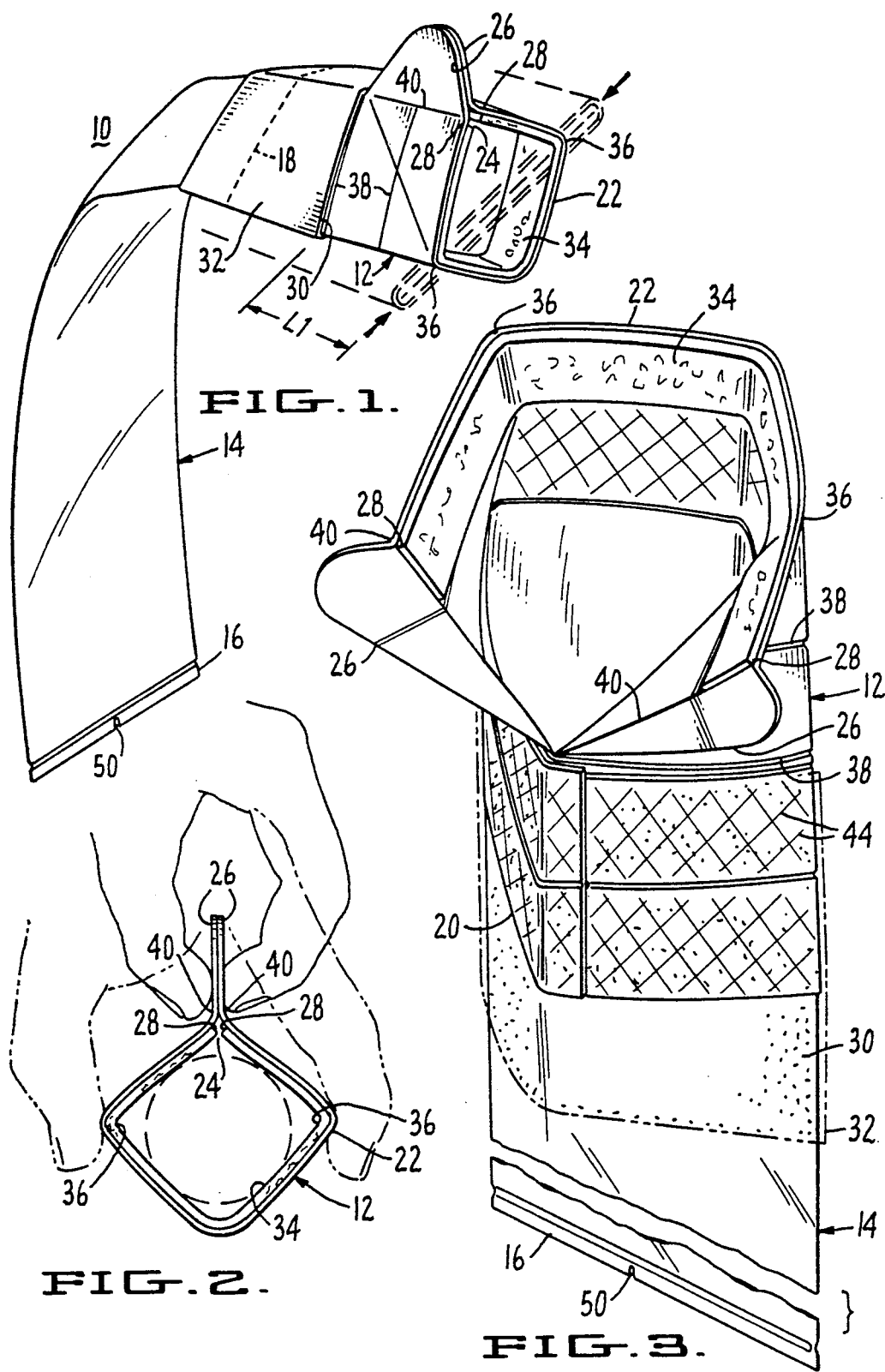

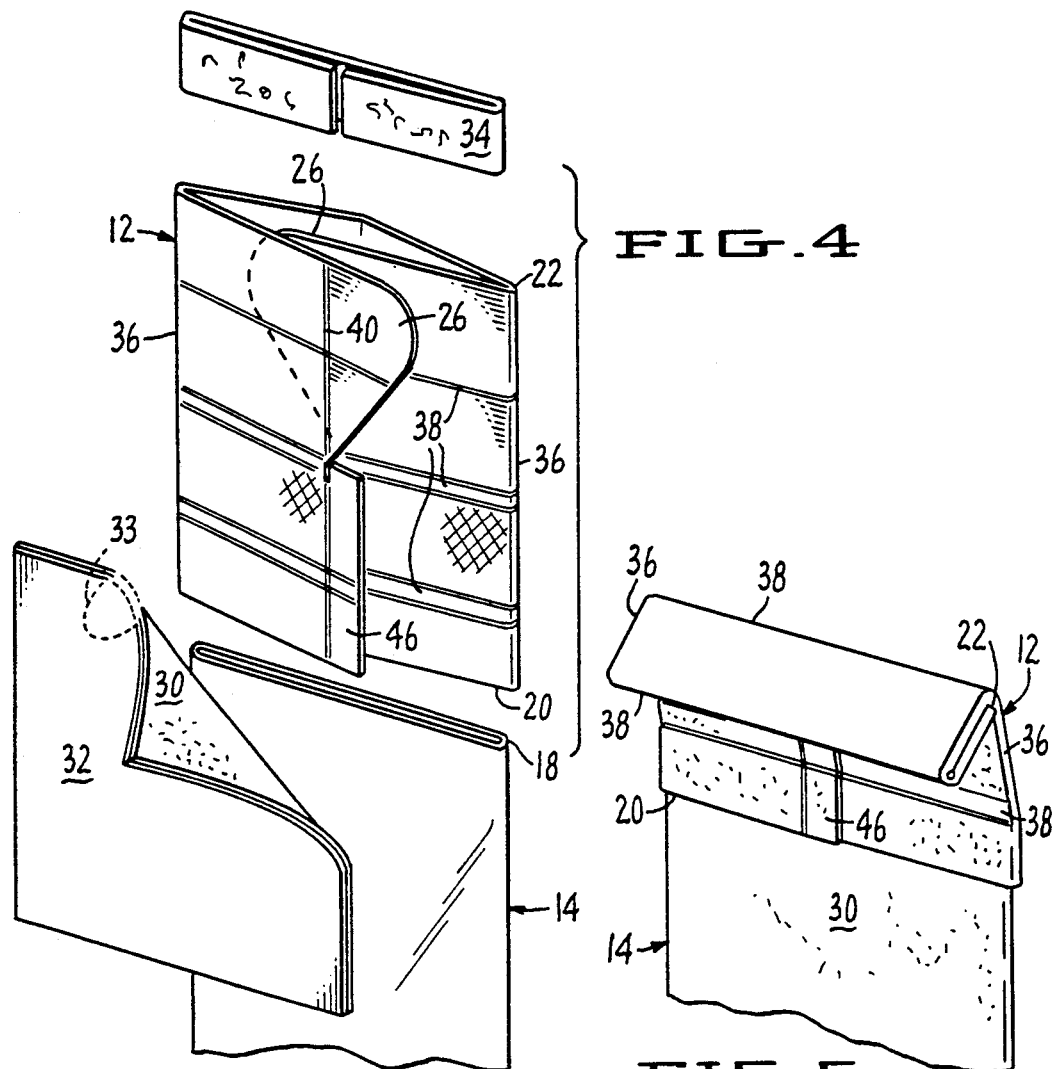

DISPOSABLE PORTABLE URINAL

BACKGROUND OF THE INVENTION

1. Field of the invention

The present invention relates to a disposable, collapsible, portable urinal, and more particularly, a male urinal.

2. Background art

In the past several years, a variety of portable urine-retaining devices have become available. A majority of these devices have been designed for medical use either to segregate a desired amount of urine for laboratory analysis, or to accommodate patients who are unable to use toilet facilities or are unable to control urine emissions. Although some of these urinal devices are disposable, few allow for compact, detached transport by the user, and none provide a self-contained method of sealing the device after use. Consequently, none of the prior art urinal devices can be discreetly and detachably carried before use while providing for sealed transport after use to a place of disposal.

In a medical facility, where permanent disposal fixtures are readily available for receiving the contents of a used portable urinal device, the need for a means of sealing the urinal after use is not acute. Likewise, in a medical facility portable urinal devices of any shape or size can be kept in convenient proximity to the patient, precluding the need for a portable urinal capable of discreet detached transport by the patient. However, where permanent disposal fixtures are not available when one has the need to urinate, a portable urinal device equipped with a means for being sealed is imperative to provide for hygienic retention of the excreted urine. Furthermore, because such a urinal device would likely be carried on one's person before use, it would be advantageous for the device to be collapsible so as to permit the device to be discreetly carried in one's pocket.

SUMMARY OF THE INVENTION

The above and other problems of prior art portable urinals are overcome by the portable urinal in accordance with the present invention which provides a more versatile portable urinal that can be collapsed to allow for discreet transport in one's pocket before use. In addition, the urinal is equipped with a sealing means to provide for hygienic retention of the excreted fluids after use.

The portable urinal of the present invention is a disposable male urinal comprising a pliable receptacle having a closed end and an opposing open end. The urinal features include a collapsible cylindrical collar having one end sealably attached along its perimeter to the perimeter of the open end of the receptacle. The opposing end of the collar has a slot through the surface of the collar. A pair of handle tabs are attached to the opposing edges of the slot.

Score lines are located in the surface of the collar in such a way as to facilitate lateral compression of the cylindrical collar into a flat square. Score lines are also positioned so as to assist rotating the handle tabs axially about the opposing edges. Score lines are additionally positioned so as to expedite separating the opposing edges outwardly from each other. Score lines running perpendicular to the axis of the cylindrical collar are so located to aid folding the flat collar upon itself. Finally, a grid of diagonal score lines is provided to add flexibility to the collar.

An adhesive material is affixed to the exterior surface of the collar along a portion of the one end of the collar. A removable protective sheet covers the adhesive material. When the protective sheet is removed and the collar is folded upon itself, that portion of the collar which comes into contact with the exposed adhesive material will be affixed to the adhesive material. In this way, a seal preventing fluid flow through the collar is created.

An absorbent strip is located on the interior surface of the collar along the perimeter of the opposing end of the collar to absorb stray fluid droplets, while also providing increased comfort to the user.

The water-impermeable material of the collar is tractable enough to permit the collar to be laterally compressed along opposing longitudinal creases until flat. At the same time, the collar material is rigid enough to expand the collar into a roughly cylindrical form when adequate pressure is applied to the exterior surface of the collar along the opposing longitudinal creases.

As will be explained in more detail herein, the disposable urinal of the present invention provides increased compact detached portability and increased ease of use over the prior art, while providing a means for sealing the urinal.

It is therefore an object of this invention to provide a urinal that is portable.

It is also an object of this invention to provide a single-use urinal that is disposable.

It is a further object of this invention to provide a urinal that is collapsible and provides compact detached portability before use.

Moreover, it is an object of this invention to provide a urinal that is inexpensive.

It is another object of this invention to provide a urinal that can be selectively adjusted to accommodate a variety of penile dimensions.

It is yet another object of the invention to provide a urinal that will expand the urine receptacle opening during use.

It is a still further object of this invention to provide a urinal that provides means for being securely sealed after use.

It is another object of this invention to provide a urinal that can be easily operated by the user with one hand.

It is yet another object of this invention to provide a urinal that is comfortable to use, while providing absorptive protection from stray fluid droplets.

It is still a further object of the subject invention to provide a urinal which allows the user to urinate in a natural manner.

It is still another object of the subject invention to provide a urinal into which the penis can be placed, rather than inserted.

It is still a further object of the subject invention to provide a urinal having no sharp edges.

It is still another object of the subject invention to provide a urinal which can be sealed in a manner to prevent leakage of fluid or odors.

BRIEF DESCRIPTION OF THE DRAWINGS

FIG. 1 is a pictorial view of the urinal showing both the expanded, as well as the collapsed configuration of the collar.

FIG. 2 is a front elevational view of the expanded collar with the handle tabs open to facilitate the placement of the penis into the collar.

FIG. 3 is a perspective view of a portion of the urinal with the collar expanded and the handle tabs raised to a vertical position.

FIG. 4 is an exploded perspective view of a portion of the urinal showing the absorbent strip, the collapsed collar with the handle tabs lowered to a horizontal position, the adhesive material layer with its protective sheet, and the open end of the receptacle.

FIG. 5 is a perspective view of a portion of the urinal showing the collapsed collar partially folded upon itself.

FIG. 6 is a view of the collar blank showing one arrangement of scoring lines.

BEST MODE FOR CARRYING OUT THE INVENTION

Referring to the figures, there is a urinal 10 comprising a collapsible collar 12 and a pliable receptacle 14. In the preferred embodiment, the collar measures 3.25"×3.5" when laterally collapsed flat. The collar is formed from paper to provide rigidity. In the preferred embodiment, the receptacle 14 consists of a plastic bag having a closed end 16 and an opposing open end 18. The collar 12 has one end 20 sealably affixed along its perimeter to the perimeter of the open end 18 of the receptacle 14.

The opposing end 22 of the collar 12 is open and includes a slot 24. In the preferred embodiment, the slot 24 extends a distance L1 of approximately 1.6". A pair of handle tabs 26 are attached to the opposing edges 28 of the slot 24. The handle tabs 26 can be axially rotated about the opposing edges 28 of the slot 24, from a horizontal position, as shown in FIG. 4, to a vertical position, as shown in FIG. 1.

An adhesive material 30 is attached to portions of the exterior surface of the collar 12 and the receptacle 14, shown in phantom line in FIG. 3. In the preferred embodiment, the adhesive material 30 consists of double stick tape. A removable protective sheet 32 covers the adhesive material 30 until the adhesive material 30 is ready to be used. The upper edge of the protective sheet 32 can be provided with a finger pull tab 33 (shown in phantom in FIG. 4) to facilitate removal of the sheet. In the alternative, the edge of the sheet can be configured to extend beyond the stick tape to define a lead liner.

The combination of a piece of double stick tape with a protective sheet is often referred to as a piggy back label. In addition to its sealing function, the double back tape also provides rigidity for maintaining the receptacle 14 in an open condition.

An absorbent strip 34 is affixed to the interior surface along a portion of the opposing end 22 of the collar 12 to provide added comfort to the user and to reduce the chances of fluid escaping from the collar 12. As shown by the figures, the absorbent strip 34 conforms to the configuration of the opposing end 22 of the collar 12.

The collar 12 can be expanded into a cylinder with one hand by applying adequate pressure with thumb and fingers simultaneously to opposing longitudinal creases 36 in the collar, as shown in FIG. 2.

FIG. 5 illustrates one way in which the collapsed collar 12 can be folded longitudinally upon itself from its opposing end 22 to bring a portion of the exterior surface of the collar 12 into contact with that portion of the exterior surface covered with the adhesive material 30.

A collar blank 13 is shown in FIG. 6 with a flap 46 attached at one end 48 of the collar blank 13. During fabrication, one end 48 of the collar blank 13 is brought into contact with the opposing end 49 of the collar blank 13 to form a cylinder having an axis parallel to the longitudinal edge of the flap 46. The flap 46 can then be affixed to that portion of the surface of the collar blank 13 overlapped by the flap 46. The upper edge of the blank is left unconnected to create slot 24.

The collar blank 13 of FIG. 6 is also shown having a preferred arrangement of score line creases impressed onto the surface of the collar blank 13. Longitudinal creases 36 expedite lateral compression of the collar into a flat configuration. Lateral creases 38 facilitate folding the flat collar 12 longitudinally upon itself from the opposing end 22 of the collar 12. Tab creases 40 enable the handle tabs 26 to be rotated axially about the corresponding opposing edges 28 of the slot 24. Hatched creases 42 aid in separating the opposing edges 28 outwardly from each other. Diagonal grid creases 44 maintain the flexibility of the collar 12 when in a cylindrical configuration.

When the urinal 10 of the invention is initially procured, the collar 12 is flat with the handle tabs 26 in a horizontal position. One handle tab 26 rests inside the opposing end 22 of the collar 12 and the other handle tab rests outside the opposing end 22 of the collar 12. The receptacle 14 is longitudinally wrapped closely around the collar 12 repeatedly for the entire length of the receptacle 14. In this configuration, the urinal 10 can be contained within a flat pouch. The pouch can fit conveniently and discreetly in a pocket, glove compartment, etc.

When use of the urinal 10 is desired, the urinal 10 is removed from the pouch and the receptacle 14 is unwrapped completely from around the collar 12. The opposing edges 28 of the slot 24 are separated outwardly, and the handle tabs 26 are rotated outward axially about the opposing edges 28. Pressure is then applied with the fingers and thumb of one hand to the exterior of the collar 12 along the opposing longitudinal creases 36, the collar 12 expands into a cylindrical configuration. Because the open end 18 of the receptacle 14 conforms to the one end 20 of the collar 12, the open end 18 of the receptacle 14 is also expanded. As noted above, the stick tape 30 will aid in maintaining the collar in the expanded condition.

Preferably, the handle tabs 26 are separated from each other along the slot 24 to define a scoop shape at the open end of the collar as shown in FIG. 3. The scoop shape is advantageous since it allows the user to place his penis into the collar rather than having to insert the penis into an opening. Insertion of the penis into an opening can be difficult if the penis is in a flaccid condition.

After the penis has been placed into the scoop of the collar, the handle tabs 26 are brought back together and oriented in the vertical position as shown in FIG. 2. The fingers and thumb can grip the handle tabs 26 to hold the collar in place throughout urination. While maintaining a grip on the handle tabs 26, the fingers and thumb can, if necessary, pinch together a portion of the opposing end 22 of the collar 12 reduce the diameter of the opposing end 22 to that which will provide a secure fit and fluid seal. In the alternative, if the penis is larger than the diameter of the collar as shown in FIG. 2, then the user can grip the tabs 26 at a higher point, allowing the diameter of the collar to expand. In this manner, a wide variety of diameters can be easily accommodated. During urination, the user's other hand is free to hold the penis and shake it off when urination is complete.

After the user's bladder has been fully relieved, the user's male member is removed. While taking care to maintain the collar 12 at a higher level than the receptacle 14, the opposing edges 28 of the slot 24 are again separated outwardly from each other. The handle tabs 26 are rotated inward axially along the opposing edges 28. The opposing edges 28 are brought back together so that the handle tabs 26 are returned to their pre-use position.

Adequate pressure is then applied to the exterior surface of the collar 12 at points other than along the longitudinal creases 36 to collapse the collar 12 flat. The protective sheet 32 is removed from the adhesive material 30. The collar 12 is then folded from the opposing end 22 of the collar 12 upon itself along the lateral creases 38 until at least a portion of the area of the adhesive material 30 affixedly receives a portion of the exterior surface of the collar 12. The urinal 10 is thereby hygienically sealed. Once the urinal is sealed in this manner, there will be no leakage and odors cannot escape.

Upon transporting the urinal 10 to a permanent disposal fixture, a corner of the closed end 16 of the receptacle 14 can be cut to allow the urine to exit from the receptacle and into the permanent disposal fixture. In the preferred embodiment, a small cut or lead 50 is formed in the end of the receptacle 14, extending part of the way into seal 16. The addition of the lead 50 allows the user to tear the bag by hand, without the need for scissors. After the urine has been emptied from the receptacle, it can be discarded into a refuse container.

The terms and expressions which have been employed here are used as terms of description and not of limitation, and there is no intention, in the use of such terms and expressions, of excluding equivalents of the features shown and described, or portions thereof, it being recognized that various modifications are possible within the scope of the invention claimed.

We claim:

1. A disposable portable urinal to accommodate a penis, comprising:
   a pliable receptacle having an interior space and provided with a closed end and an opposing open end;
   a pliable, collapsible cylindrical collar with the perimeter of one end thereof being sealably attached to the open end of the receptacle, and with the opposing end of the collar having a slot extending axially therefrom to a point intermediate the length of the collar; and
   a pair of handle tabs for gripping the collar attached to opposing edges of the slot such that the handle tabs can be used to separate the collar along the slot allowing the penis to be placed within the collar whereupon the handles are used to compress the collar around the penis to prevent leakage.

2. The device as described by claim 1, wherein the collar is formed from paper material having a plurality of score lines to add flexibility.

3. The device as described in claim 1, wherein an absorbent strip is affixed to the interior of the collar along the perimeter of the opposing end.

4. The device as described by claim 1, wherein the handle tabs are arcuate.

5. The device as described in claim 1, including a means for sealing the collar.

6. The device as described by claim 5, wherein the means for sealing the collar includes an adhesive material attached to the exterior surface of the collar, such that the collar can be folded upon itself and into sealing contact with the adhesive material.

7. The device as described by claim 6, wherein the means for sealing the collar further includes at least one score line in the surface of the collar positioned so as to expedite folding the collar into sealing contact with the adhesive material.

8. The device as described by claim 6, wherein the adhesive material is covered by a removable protective sheet.

* * * * *